US010226562B2

(12) United States Patent
Schulte et al.

(10) Patent No.: US 10,226,562 B2
(45) Date of Patent: Mar. 12, 2019

(54) METHOD FOR THE DETERMINATION OF AT LEAST ONE CHARACTERISTIC FIGURE RELATING TO A PATIENT'S GLUCOSE METABOLISM, AND APPARATUS THEREFOR

(75) Inventors: Elke Schulte, Schweinfurt (DE);
Carsten Müller, Euerbach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 409 days.

(21) Appl. No.: 12/742,415

(22) PCT Filed: Nov. 11, 2008

(86) PCT No.: PCT/EP2008/009501
§ 371 (c)(1),
(2), (4) Date: Aug. 4, 2010

(87) PCT Pub. No.: WO2009/062661
PCT Pub. Date: May 22, 2009

(65) Prior Publication Data
US 2010/0298751 A1    Nov. 25, 2010

(30) Foreign Application Priority Data

Nov. 12, 2007 (DE) .......... 10 2007 053 752

(51) Int. Cl.
*A61M 37/00* (2006.01)
*A61M 1/34* (2006.01)
(Continued)

(52) U.S. Cl.
CPC ......... *A61M 1/342* (2013.01); *A61B 5/14532* (2013.01); *A61M 1/1609* (2014.02);
(Continued)

(58) Field of Classification Search
CPC .............. A61M 2230/201; A61M 1/34; A61M 5/1723; A61M 1/342; A61M 1/1609;
(Continued)

(56) References Cited

U.S. PATENT DOCUMENTS 4,266,021 A   5/1981 Nylen et al.
4,318,401 A   3/1982 Zimmerman
(Continued)

FOREIGN PATENT DOCUMENTS

DE    2853897    6/1979
DE    3153686    1/1992
(Continued)

OTHER PUBLICATIONS

PCT International Search Report for PCT/EP08009501 dated Mar. 6, 2009.
(Continued)

*Primary Examiner* — Andrew J Mensh
(74) *Attorney, Agent, or Firm* — Fish & Richardson P.C.

(57) ABSTRACT

The present invention relates to a method for detecting at least one characteristic relating to a patient's glucose metabolism, having steps to be performed during an extracorporeal treatment of the patient's blood, particularly during a dialysis treatment, of the extracorporeal addition of glucose and/or insulin and extracorporeal measurement of a glucose concentration and/or an insulin concentration. The invention further proposes a corresponding device. In addition, the invention proposes a method for determining the composition of the dialysate for the extracorporeal treatment of a patient's blood having the steps of determining a glucose level in the patient's blood during the dialysis session and adapting the amount of glucose added to the dialysate or blood based on the glucose level determined. To
(Continued)

this end, the invention proposes a corresponding device. The invention further proposes a blood treatment device.

28 Claims, 2 Drawing Sheets

(51) Int. Cl.
    *A61B 5/145*     (2006.01)
    *A61M 1/16*     (2006.01)
    *A61M 1/00*     (2006.01)
    *B01D 11/00*     (2006.01)
    *C02F 1/00*     (2006.01)
    *G01N 33/48*     (2006.01)
    *C12Q 1/54*     (2006.01)
    *A61M 5/172*     (2006.01)
    *B01D 61/32*     (2006.01)

(52) U.S. Cl.
    CPC ........ *A61M 1/3434* (2014.02); *A61M 1/3437* (2014.02); *A61M 1/3458* (2014.02); *A61M 1/34* (2013.01); *A61M 5/1723* (2013.01); *A61M 2230/201* (2013.01); *B01D 61/32* (2013.01); *C12Q 1/54* (2013.01)

(58) Field of Classification Search
    CPC .............. A61M 1/3434; A61M 1/3437; A61M 1/3458; A61B 5/14532; B01D 61/32; C12C 1/54
    USPC ..... 604/4.01, 6.09, 5.04, 316; 210/645, 646, 210/739; 356/39
    See application file for complete search history.

(56) References Cited

U.S. PATENT DOCUMENTS

| | | | |
|---|---|---|---|
| 4,469,593 A * | 9/1984 | Ishihara | A61M 1/16 210/104 |
| 5,341,805 A * | 8/1994 | Stavridi et al. | 600/316 |
| 5,670,057 A * | 9/1997 | Chen et al. | 210/739 |
| 5,995,860 A * | 11/1999 | Sun et al. | 600/341 |
| 6,027,692 A * | 2/2000 | Galen et al. | 422/82.05 |
| 6,925,393 B1 | 8/2005 | Kalatz et al. | |
| 2004/0110693 A1* | 6/2004 | Trepel | A61K 31/133 514/25 |
| 2006/0009727 A1 | 1/2006 | O'Mahony et al. | |
| 2006/0200064 A1 | 9/2006 | Gross et al. | |
| 2007/0023334 A1 | 2/2007 | Hallstadius et al. | |
| 2007/0225675 A1* | 9/2007 | Robinson | A61B 5/14532 604/504 |
| 2009/0012376 A1 | 1/2009 | Agus | |
| 2010/0298751 A1 | 11/2010 | Schulte et al. | |

FOREIGN PATENT DOCUMENTS

| | | |
|---|---|---|
| DE | 69025646 | 9/1996 |
| DE | 102 12 247 C1 | 12/2003 |
| EP | 0330892 | 9/1989 |
| EP | 0401179 | 12/1990 |
| EP | 0678301 | 10/1995 |
| EP | 1 348 457 C1 | 10/2003 |
| EP | 1872812 | 1/2008 |
| JP | 54-092300 A | 7/1979 |
| JP | 2001204817 | 7/2001 |
| WO | WO 97/44072 | 11/1997 |
| WO | WO 98/19592 | 5/1998 |
| WO | WO 2004/089440 | 10/2004 |
| WO | WO2005/028001 | 3/2005 |
| WO | WO 2005/044088 | 5/2005 |
| WO | WO 2005044088 A2 * | 5/2005 |
| WO | 2006-029293 A1 | 3/2006 |

OTHER PUBLICATIONS

Giessauf et al., "Glucose Uptake and Elimination Following an Intra-Dialytic Glucose Load", XLIV ERA-EDTA, Jun. 21-24, 2007, Barcelona, Spain.

Japanese Search Report by Registered Searching Organization in Japanese Application No. 2010-532504, dated Jul. 25, 2012, 11 pages (with English translation).

* cited by examiner

METHOD FOR THE DETERMINATION OF AT LEAST ONE CHARACTERISTIC FIGURE RELATING TO A PATIENT'S GLUCOSE METABOLISM, AND APPARATUS THEREFOR

CROSS-REFERENCE TO RELATED APPLICATIONS

The present application is the national stage entry of International Patent Application No. PCT/EP2008/009501, filed on Nov. 11, 2008, and claims priority to Application No. DE 10 2007 053 752.4, filed in the Federal Republic of Germany on Nov. 12, 2007.

FIELD OF THE INVENTION

The present invention relates to a method for the determination of at least one characteristic figure relating to a patient's sugar metabolism. It further relates to a corresponding apparatus and to a treatment apparatus.

The present invention further relates to a method for defining the composition of a dialysate for dialysis and to a corresponding apparatus.

BACKGROUND

In recent years, the glucose metabolism and particularly the treatment of elevated blood sugar values has increasingly become the focus of attention of the persons in authority, owing to the gravity of disorders following in the wake of elevated blood sugar values, and not least also because of the related, immense costs for the healthcare system. Considering the fact that the glucose metabolism is as yet not fully understood, it is not surprising that new study protocols on the future scientific investigation of glucose metabolism are being regularly published up to the present day, as again recently in the congress paper "*Glucose Uptake and Elimination Following an Intra-Dialytic Glucose Load*" by Giessauf et al. on the occasion of XLIV ERA-EDTA, Jun. 21 to 24, 2007, in Barcelona, Spain.

Diagnosis of a manifest diabetes mellitus is nowadays possible in a comparatively simple manner. What presents more difficulty is to furthermore recognize preliminary stages of a diabetes mellitus not clinically manifest yet, that are accompanied by an impaired glucose tolerance.

From practice, methods for the determination of a person's glucose tolerance and/or insulin resistance are known. These methods serve for the recognition and differentiation of an impaired glucose homeostasis ("impaired fasting glucose") or of a diabetes mellitus, respectively. To this end, blood parameters are initially determined for the person in question. Based on the measured blood parameter values on the one hand and the entirety of circumstances that might jointly have influenced the measurement values on the other hand, the physician may diagnose a possibly existing impaired glucose homeostasis.

The circumstances that must not be left out of consideration in such a diagnosis include, inter alia, whether the patient had been fasting or post-prandial at the time when the blood sugar values were taken, how much time had passed since a glucose administration for testing purposes, whether the patient is running a temperature, whether the patient ingested a minimum amount of carbohydrates over the past few days, and whether the patient is on medication.

In case of medicament ingestion, those medicaments which are apt to influence the blood sugar level are particularly of relevance. Such medicaments include, e.g., corticoids, contraceptives, or oral antidiabetics. But the physician also has to elucidate whether, e.g., insulin other than endogenous insulin was administrated. Such intake not in connection with a prescription by a physician may regularly be observed with persons having an explicit desire to lose weight. Lastly, the circumstances to be taken into account by the physician when diagnosing a pathological glucose tolerance also include disorders that have a bearing on the production or secretion of insulin.

The blood sampling necessary in the performance of a glucose tolerance test following oral intake of glucose is felt by some patients to be unpleasant.

As diabetics are, as a general rule, also dialysis patients as a consequence of their sugar metabolism, it is proposed in PCT Publication No. WO 98/19592 to perform the blood glucose or blood sugar level measurement during one dialysis session by way of the dialysis apparatus. As an access to vessels of the patient's has in any case already been placed for the purposes of the dialysis treatment, it is possible to determine current blood sugar values through the method described in PCT Publication No. WO 98/19592 without separately having to take blood for this purpose.

A pathological glucose homeostasis in which the blood sugar values may be measured to be bordering on the hazardous cannot, however, be identified by the method described in PCT Publication No. WO 98/19592. Performance of a dialysis, which results—and is intended to result—in a modified composition of the blood to be treated, may moreover have a negative influence on the blood sugar measurement and result in inaccuracies of the measured blood glucose values.

The present invention has the object of providing an improved method for examining a patient's sugar metabolism and particularly for the determination of characteristic figures relating to the patient's blood sugar, as well as a corresponding apparatus.

SUMMARY

In accordance with the invention, a method is proposed whereby at least one characteristic figure or a parameter value or a pattern of a parameter relating to a patient's glucose or sugar metabolism may be determined. The method includes an extracorporeal addition of blood sugar and/or insulin during an extracorporeal treatment of the patient's blood as well as an extracorporeal measurement of a glucose concentration and/or an insulin concentration.

In accordance with the invention, a characteristic figure for characterization of the sugar metabolism is understood to be a blood sugar concentration, an insulin concentration, a development of the above mentioned concentrations over time, as well as any other characteristic figure suited to furnish the skilled person with a relevant indication of the patient's sugar metabolism and particularly of a pathological condition thereof.

In accordance with the invention, sugar metabolism or glucose metabolism is understood to be the carbohydrate metabolism in general. The invention shall therefore be restricted to neither the administration nor the measurement of glucose as a sugar. Any other sugar, the blood concentration of which is relevant in the context of the present invention for a statement whether or not a patient is, for instance, a diabetic or exhibits a pathological glucose tolerance, is equally encompassed by the term sugar or glucose metabolism as used in the present patent application. This applies irrespective of the synonymous use of the expressions glucose and sugar hereinafter.

In the framework of the invention, an extracorporeal addition of glucose and/or insulin is understood to be the addition thereof into the equipment used for the extracorporeal treatment of a patient's blood. This equipment includes particularly the arterial and venous conduit(s) of an extracorporeal circulation. The term equipment further encompasses, in addition to dialysis apparatuses, other devices for the extracorporeal treatment of blood, e.g., heart-lung-machines. The addition of glucose or insulin may thus, in accordance with the invention, also take place during an extracorporeal blood treatment serving purposes other than those of dialysis. The same applies to the measuring step. In the case of a dialysis, the equipment additionally includes the dialysate or the substituate—where substitution is provided—as well as any other conduits and components of the device employed for dialysis—irrespective of whether, e.g., for hemodialysis, hemofiltration or hemodiafiltration.

In accordance with the invention, the term "extracorporeal" designates a parenteral administration in connection with the administration of glucose and/or insulin. This may take place manually by way of syringe, automatically by means of infusion pump or perfusor, into a previously existing vascular access which encompasses, in accordance with the invention, in particular the entire apparatus for blood treatment including conduit and tubing system.

In connection with measurement of the glucose and/or insulin concentration, the expression "extracorporeal" is understood in the context of the present invention as a measurement which does not separately require the placement of an access, but rather a previously existing vascular access for the purpose of the blood treatment performed in parallel, which access in accordance with the invention in particular also encompasses a venous or arterial conduit or tubing system for the blood treatment. It is expressly pointed out that even a non-invasive measurement, for instance through the patient's skin by means of an optical method out of contact with the blood, and likewise a measurement of a concentration in the dialysate, is assumed to be extracorporeal in the framework of the invention.

The glucose concentration measurement may take place at predetermined times during the patient's extracorporeal treatment, for instance at the beginning of a dialysis treatment, cyclically, or upon demand by the user. It may, however, also take place continually.

Where the glucose concentration and/or the insulin concentration in the patient's extracorporeally flowing blood is measured, this is a determination of the concentration in the patient's blood. In accordance with the invention, however, the expression "measuring the glucose concentration and/or the insulin concentration" is moreover understood, for instance, as a measurement of a quantity of glucose passing through a filter, or by which the quantity of a blood sugar present in a dialysate changes. The fact that such "quantities" of blood sugar or insulin may generally also be expressed in terms of concentrations, and that the invention thus covers a measurement both of quantities and of concentrations, will be understandable to the skilled person without any further explanation.

Measurement of the glucose concentration and/or insulin concentration may take place by means of one or several sensors in the extracorporeal blood circulation. In the case of a dialysis treatment of the patient, it is moreover also possible to perform a measurement on the dialysate side (in addition to further measurements or exclusively), for glucose may pass through the filters that are customary in dialysis treatments.

For a measurement of the blood sugar concentration, and particularly of the blood sugar level of a patient, various methods are conceivable. These include enzymatic methods, optical methods such as absorption, polarization or spectroscopy, measurement of osmotic changes, measurement of changes of conductivity, as well as other methods known to the skilled person.

In accordance with the invention, "measurement" is also understood to be an extracorporeal taking of blood—e.g., via a component of the apparatus for blood treatment—and supplying the taken sample to a corresponding laboratory. The laboratory may be located externally. The laboratory may, however, also be provided in the apparatus for blood treatment, or co-operate with the latter at the location of the patient's treatment.

The method of the invention is characterized, inter alia, by the fact that due to the extracorporeal and thus parenteral administration of glucose and the resulting circumvention of the digestive tract, a recognition of a possibly existing impaired glucose tolerance possible, which is independent of the kinetics and of possibly existing impairments of the uptake of glucose by the digestive organs, and which thus is more accurate.

Thanks to the utilization of the accesses already existing for the extracorporeal treatment of the blood (for which even a single access would be sufficient), however, a separately placed intravenous access is not required in contrast with the performance of an—advantageously—non-oral glucose tolerance test. The method of the invention is thus more gentle and above all less unpleasant to the patient. Moreover the risk of an infection is advantageously reduced through the fact that it is not necessary to place an additional access.

It is another advantage of the method of the invention that the measurements required for the glucose tolerance test may take place in parallel with a therapy taking place, anyway. The patient therefore does not need to take extra time for the performance of the method of the invention. Rather, this takes place during the time which the patient will in any case spend for the performance of the extracorporeal blood treatment either in the hospital or clinic or, in the case of home dialysis, on the treatment unit.

As the method of the invention may, however, take place on the side, as it were, requires neither additional time nor effort on the part of the patient, and furthermore does not involve any additional inconvenience, some patients' degree of reluctance against having their glucose metabolism examined is incomparably less with application of the method of the invention than with customary methods.

By means of the method of the invention used for measuring characteristic figures, an impaired glucose tolerance may therefore be recognized clearly earlier on than would be the case in a traditional performance involving persuasion of the patient by the attending physician and making an appointment for the patient, which is frequently difficult. An earlier start of reducing the future blood sugar intake and an earlier lowering of the blood sugar level in the future so as to prevent, or at least delay, the occurrence of (follow-up) disorders which are known to be brought about by elevated blood sugar, is therefore advantageously also possible due to the utilization of the method of the invention.

In a balanced variation of the blood glucose concentration or of the extracorporeally added quantity of glucose addition, the present method furthermore enables a measurement or determination of the current blood volume as well as a simplified recirculation measurement, which is regularly of interest for the purpose of monitoring a correct performance of the extracorporeal blood treatment.

It should be noted that the method of the invention may advantageously also be utilized for the examination of endocrinal impairments accompanying a pathological secretion of insulin as described at the outset.

Advantageous developments of the present invention are described herein.

In a preferred embodiment it is thus proposed to change the concentration of sugar, or glucose, in the dialysate—i.e., the glucose customarily added to a dialysate liquid for the treatment of the patient when composing said dialysate liquid—based on the measured glucose concentration, and particularly based on a measured blood sugar level. Such changing may take place continuously or at specific times.

By means of this changing, where performed within the meaning of adapting the glucose concentration of the dialysate to that of the blood, a shift of blood sugar across the dialysis filter may advantageously be minimized or even prevented. Therefore, an increase in blood sugar following the extracorporeal administration of glucose may be determined correctly, namely, without the measurement result being falsified by the shift of glucose from the blood through the dialysis filter into the dialysate. Using a different expression, the dialysate glucose concentration is assimilated to the blood glucose concentration.

After the tolerance test—but where necessary also as early as in the course of its performance—a corresponding adaptation, i.e., a change within the meaning of lowering may, however, also effect a rapid return of the blood sugar level to a standard value after administration of glucose. Moreover, it may advantageously be ensured that a predetermined, maximum blood sugar value cannot even be reached. Hyperglycemia is hereby advantageously avoided in accordance with the invention.

The at least one characteristic figure may be determined while reflecting the change of the dialysate glucose concentration in order to avoid a glucose shift across a filter—or based thereon—as is provided in another further preferred embodiment of the method of the invention. In this way, the process of extracorporeally measuring the blood sugar level may at least partly be omitted or advantageously be simplified.

In another further preferred embodiment of the method of the invention, it is provided to allow for a blood sugar shift across a dialysis filter after the extracorporeal addition of blood sugar and to determine a measure for the shift having taken place. The at least one characteristic figure may be determined while reflecting the glucose shift across the filtering means—or based thereon.

This technique is advantageously characterized in that on the one hand, a more accurate and more correct determination of the desired characteristic figure may take place, inasmuch as a blood sugar shift detrimental to this determination is compensated or reflected by calculatory means. In addition, this embodiment of the method of the invention is also characterized through the fact that it does not require an adaptation of the dialysate concentration on the apparatus side, as is described for other embodiments. It is rather sufficient to carry out a calculatory reflection or "correction" of the measured glucose concentration by means of the known glucose shift across the filter when determining the characteristic figure.

The latter results in a simplification in terms of equipment and thus in a reduction of the required production costs for an apparatus intended for the performance of the method of the invention. It moreover results in further reduced expense for servicing and maintenance while reducing the related costs and the required amount of time.

Another further preferred example embodiment according to the invention of the above described method provides an extracorporeal addition of sugar and/or insulin on the dialysate side or on the substituate side—where a substituate is provided. The addition of sugar and/or insulin may take place partly or entirely on the dialysate side and/or on the substituate side. This requires particularly low technical complexity, allows for an altogether simplified construction, and thus contributes to saving costs. Here it is also an advantage that a location of addition on the arterial or venous side is not required. A connection to the extracorporeal blood circulation for the addition of glucose and/or insulin may thus advantageously be omitted. This contributes to avoiding infections as well as leakages from the blood circulation. The addition of glucose and/or insulin on the dialysate side moreover advantageously allows a more accurate control of the addition. The addition may moreover take place more continuously than in the case of an addition on the blood side, for example with a syringe pump, and particularly at an equivalent technical complexity. The addition may take place with the aid of a dedicated means. This means may be employed in addition to a means for producing and/or adding dialysate which is employed for treating the patient. It may be provided for examining the glucose metabolism. It may expressly not at the same time be provided for the treatment of the patient subject to dialysis. Nevertheless, the means may be functionally and/or structurally connected to a means for producing dialysate and/or adding glucose into the dialysate for the treatment of the patient subject to dialysis in order to obtain synergies, avoid additional technical complexity, etc. Thus, for the purpose of examining the glucose metabolism, the means for adding glucose and/or insulin may be realized by a (closed- or open-loop) control allowing an addition of glucose or insulin that is different from the addition of glucose to the dialysate. The (closed- or open-loop) control may be part of the conventional means for producing a dialysate by using glucose. The addition of glucose for examining the metabolism may take place in the form of a bolus. It may also take place in the form of an—at least temporarily—increased addition of glucose to the dialysate.

In accordance with another further preferred embodiment according to the invention, the method includes an automated performance of at least one step of the method of the invention. This step may in particular be the addition of glucose and/or insulin. It may, however, also relate to measurement of the glucose concentration and/or insulin concentration with the aid of respective suitable means or mechanism.

The advantages in this context include in particular a reduced workload for the attending physician, the obtainment of enhanced accuracy in the performance of the glucose tolerance test, e.g., through the accurate observation of time intervals between single steps or measurements in the performance of the tolerance test. A further advantage resides in an exact repeatability of the examination conditions.

In each one of the above-mentioned example embodiments of the method of the invention, this may include an outputting or displaying and/or storing of at least one determined characteristic figure. In outputting, the information obtained through the measurement may be furnished to the user graphically (e. g., as a plotted curve) or in the form of numeric values on paper or monitor. A transmission of the data to other apparatus (so-called "telemonitoring") may furthermore take place. Storing, inter alia, serves for documentation later on, as well as for a comparison with further test results of measurements and other examinations carried out previously or later on. It may take place by means of customary storage media.

The object of the invention is moreover attained through an apparatus for the determination of at least one characteristic figure. Advantageous developments in turn are subject matter of the subclaims. All of the advantages that may be obtained by the method of the invention described herein are also obtained undiminished by the apparatus. In order to avoid repetitions, explicit reference is therefore made to the above discussed advantages.

The present invention furthermore has the object of specifying an improved method for defining the composition of the dialysate as well as a corresponding apparatus.

This object of the invention is achieved through example embodiments of the method described herein.

It is therefore proposed, in accordance with the invention, to determine the blood glucose level during the dialysis session in order to define the composition of the dialysate for a dialysis treatment of the patient. This determination may take place extracorporeally in accordance with the above description, but also intravenously. Furthermore, the glucose quantity to be added to the dialysate is adapted on the basis of the determined blood glucose level. Thus, an ideal blood sugar adjustment is possible at least for the duration of the dialysis treatment. It is hereby made possible to avoid a dropping blood sugar as a consequence of glucose deficiency and to obtain a stabilization of the patient.

It is to be noted expressly that this method of the invention may also be employed wherever glucose is added to the patient on the occasion of an extracorporeal blood treatment. The method is therefore not restricted to its application in the treatment of patients subject to dialysis.

This object of the invention is also achieved through example embodiments of the apparatus described herein. As the same advantages may be obtained hereby as by the method of the invention, reference is once again made to the above discussion in order to avoid repetitions. For example, the objects of the invention may be achieved through a blood treatment apparatus, particularly a dialysis apparatus as disclosed herein and having the above discussed advantages. The blood treatment apparatuses disclosed herein may be, e.g., a conventional blood treatment apparatus, particularly a known dialysis apparatus.

The present invention shall now exemplarily be explained in more detail by way of the following example.

Thus, during a dialysis session or during any other extracorporeal blood treatment, a particular quantity of glucose—for instance 0.5 grams/kilogram of body weight—may be added to a patient within a predetermined time window of, e.g., 2 minutes via the venous branch of the extracorporeal circulation. This does not require a separately placed access while the tolerance test may nevertheless be performed parenterally with the respective known advantages.

Characteristic figures for evaluation of the glucose tolerance may be calculated from the development of the blood sugar curve. This may, for example, be the k value resulting from $k=\ln 2/T_{1/2}*100$, where $T_{1/2}$ designates the half-value time of glucose. Following an elucidation of any further factors of influence that are also relevant for the physician and were named at the outset, a value for k of greater than 1.2 may herein be an indication of a physiological glucose tolerance, whereas a value for k of less than 1.0 may point to an impaired glucose tolerance.

As an alternative, the period of time which passes until significant values—e.g., the base value—are reached, may be determined and subsequently evaluated by the physician. In diabetics, this may amount to more than 80 minutes, in a healthy person 40 to 70 minutes following the injection of 15 grams of glucose/$m^2$ of body surface (ivGTT according to Dérot). In addition to glucose kinetics, the insulin level in the blood may be measured and evaluated. Measurement of the insulin concentration may optionally take place on the machine side or be determined by the user in the laboratory. The apparatus employed for carrying out the method of the invention may provide the user with signals for sample-taking after previously set time intervals, or in turn take measurements autonomously or automatically.

It is to be noted that instead of a short-term, high dose of glucose, a prolonged glucose infusion via the extracorporeal circulation and/or the dialysate may equally take place, and that the glucose and/or insulin values may be measured concurrently.

The present invention is additionally explained in further detail by means of the drawings in which same reference numerals designate same or identical components.

DETAILED DESCRIPTION

Figure 1:
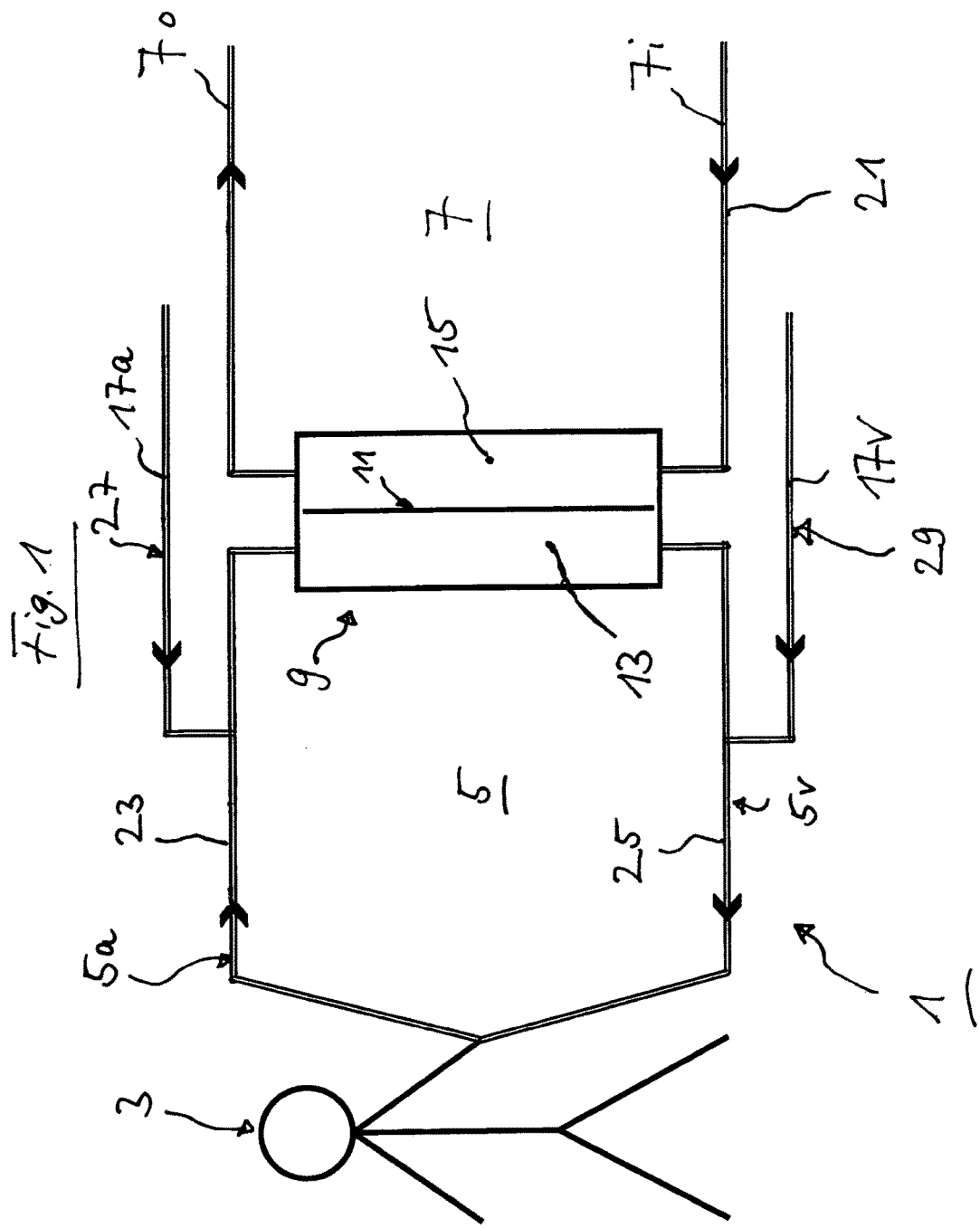
FIG. 1 shows in schematically simplified representation an extracorporeal blood circulation comprising addition points for glucose and/or insulin in accordance with an example embodiment of the present invention.

FIG. 1 shows in schematically simplified representation an extracorporeal blood circuit or circulation 1 for the treatment of a patient 3, wherein the blood circulation 1 includes an extracorporeal circuit or circulation 5 as well as an incompletely represented dialysate circuit 7. Both the extracorporeal circulation 5 and the dialysate circuit 7 flow into a dialyzer 9 and out thereof again. The dialyzer 9 includes a dialyzer membrane 11 which is disposed between a blood chamber 13 and a dialysate chamber 15 and performs a filtering function.

The extracorporeal circulation 5 includes an arterial branch 5a and a venous branch 5v. The dialysate circuit 7 includes a branch 7i for the dialysate supply and a branch 7o for the dialysate discharge.

In the blood circulation 1 of FIG. 1 there is moreover provided an incompletely represented substituate supply, or a predilution conduit 17a entering on the arterial side of the extracorporeal blood circulation in branch 5a, and an equally incompletely represented substituate supply, or a post-dilution conduit 17v, which merges into the venous branch 5v of the extracorporeal circulation 5. The substituate supplies 17a and 17v are optional and not provided universally.

The arrows inserted in FIG. 1 indicate the respective flow directions in the associated branches or conduits, respectively.

In FIG. 1, five possible points for an injection of glucose and/or insulin are moreover entered. These points are designated as 21, 23, 25, 27, and 29. In point 21 the glucose or the insulin may be added to the dialysate, in point 23 the named substances may be added to the extracorporeal circulation 5 upstream of the dialyzer 9, in point 25 to the extracorporeal blood circulation 5 downstream of the dialyzer 9. In point 27, the substances are added to the substituate supply on the arterial side and in point 29 to the substituate supply on the venous side. Such addition may take place by means of one or several respective means (not represented).

Figure 2:
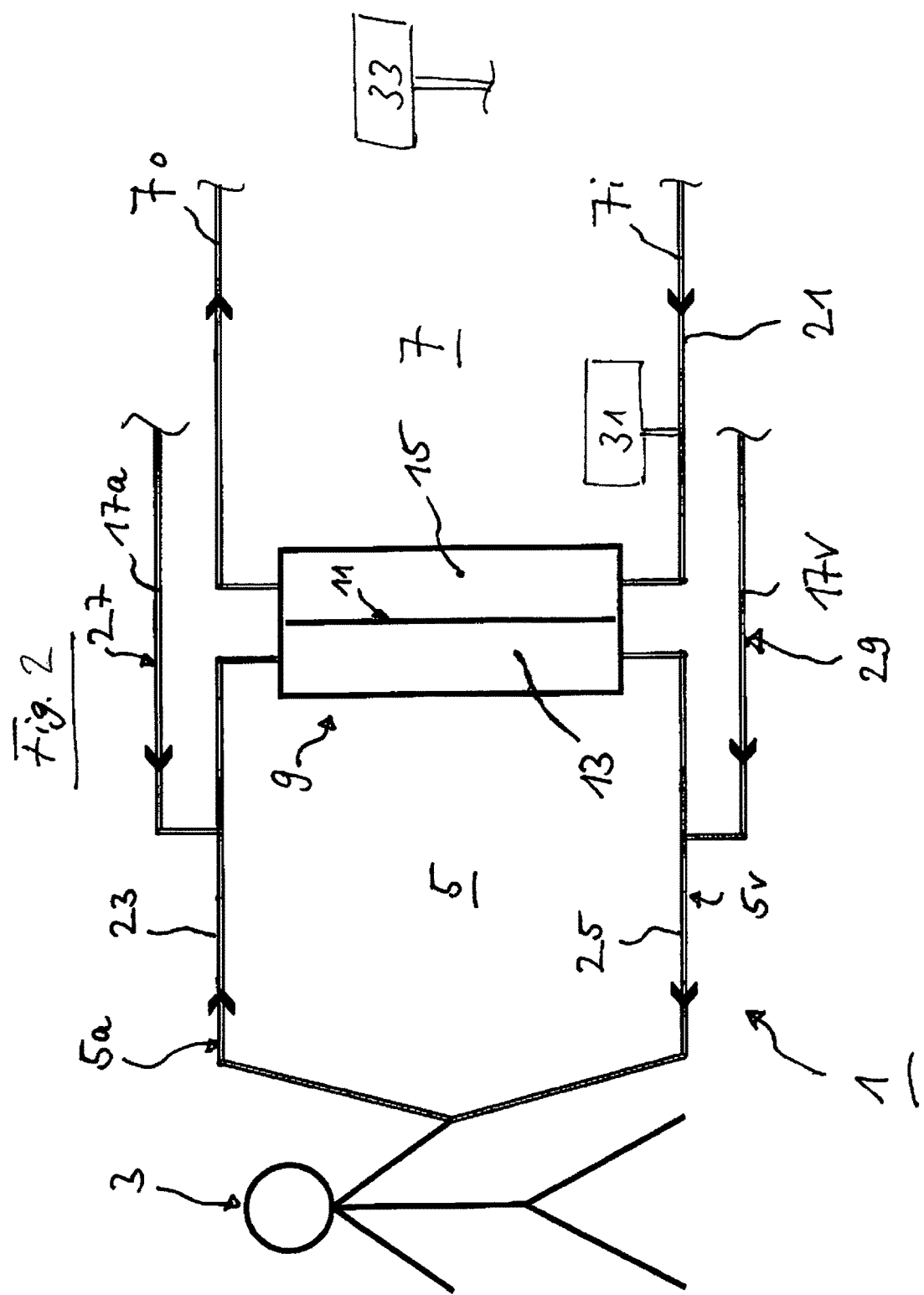
FIG. 2 shows the blood circulation of FIG. 1 with additional structure.

FIG. 2 shows the blood circulation of FIG. 1. FIG. 2 additionally shows a means 31 whereby glucose may be added to the extracorporeal circuit for the purpose of examining the glucose metabolism. The location of addition in FIG. 2 is only one of the possible locations of addition.

FIG. 2 furthermore shows a means 33 for adding glucose to a dialysate liquid or to a dialysate for treating the patient 3, as is known from the prior art. The means 31 and 33 may be connected to each other in an appropriate manner. It is also conceivable for one means to assume the functions of both means 31 and 33. For this it must be prepared in a suitable manner.

The present invention thus for the first time proposes a method for the determination of at least one characteristic figure relating to a patient's glucose metabolism, including the steps to be performed during an extracorporeal treatment of the patient's blood, particularly during a dialysis treatment, of extracorporeal addition of glucose and/or insulin and extracorporeal measurement of a glucose concentration and/or an insulin concentration. It moreover specifies a corresponding apparatus. In accordance with the invention, a method for defining the composition of the dialysate for the extracorporeal blood treatment of a patent is moreover proposed, including the steps of determining a glucose level in the patient's blood during the dialysis session, and adaptation of the glucose quantity to be added to the dialysate or to the blood based on the determined glucose level. For this purpose a corresponding apparatus is specified. In addition, a blood treatment apparatus is proposed.

The invention claimed is:

1. A method, comprising:
    starting a hemodialysis, hemofiltration, or hemodiafiltration treatment of a patient using a blood treatment apparatus, a dialysate circuit, and an extracorporeal blood circuit;
    adding, during the treatment, a particular quantity of glucose to the extracorporeal blood circuit to mix with blood of the patient;
    after the adding, measuring glucose concentration values at different points in time during the treatment, wherein the measuring is performed at least in part by one or more sensors measuring the blood of the patient at one or more locations along the extracorporeal blood circuit;
    adjusting, during the treatment, a glucose concentration of a dialysate liquid within the dialysate circuit such that a glucose shift across a dialysis filter is reduced;
    characterizing, using the blood treatment apparatus, the patient's metabolization of the particular quantity of glucose based on: (i) the measured glucose concentration values, (ii) the different points in time that the glucose concentration values were measured, and (iii) the particular quantity of glucose added to the extracorporeal blood circuit;
    outputting, using the blood treatment apparatus, a result of the characterizing; and
    detecting diabetes or a pathological glucose tolerance of the patient based on the result of the characterizing.

2. The method according to claim 1, further comprising: changing the glucose concentration of the dialysate liquid while monitoring the measured glucose concentration.

3. The method according to claim 2, wherein a change in the glucose concentration of the dialysate liquid is used to determine at least one characteristic figure relating to the patient's metabolization of the particular quantity of glucose.

4. The method according to claim 1, wherein the characterizing the patient's metabolization of the particular quantity of glucose includes determining a glucose shift across the dialysis filter after the extracorporeal addition of glucose, wherein the glucose shift across the dialysis filter is used to determine at least one characteristic figure relating to the patient's metabolization of the particular quantity of glucose.

5. The method according to claim 1, wherein the extracorporeal addition of glucose includes an addition on at least one of a dialysate side and on a substituate side.

6. The method according to claim 1, wherein at least one of a) the addition of the particular quantity of glucose and b) the measuring of the glucose concentration values is automated.

7. The method according to claim 1, wherein the adjusting the glucose concentration of the dialysate liquid comprises:
    adjusting the glucose concentration of the dialysate liquid within the dialysate circuit in coordination with the measured glucose concentration of the blood of the patient such that the glucose shift across the dialysis filter is reduced.

8. A method, comprising:
    starting a hemodialysis, hemofiltration, or hemodiafiltration treatment of a patient using a blood treatment apparatus, a dialysate circuit, and an extracorporeal blood circuit;
    adding, during the treatment, a particular quantity of at least one of a) glucose and b) insulin to the extracorporeal blood circuit to mix with blood of the patient;
    after the adding, measuring at different points in time during the treatment a concentration of at least one substance comprised of at least one of a) glucose and b) insulin, wherein the measuring is performed at least in part by one or more sensors measuring the blood of the patient at one or more locations along the extracorporeal blood circuit;
    adding, during the treatment, at least one of a) glucose and b) insulin to the dialysate circuit such that a glucose shift or an insulin shift across a dialysis filter is reduced;
    characterizing, via the blood treatment apparatus, the patient's metabolization of the particular quantity of the at least one of a) glucose and b) insulin by evaluation of a curve over time that is based on: (i) the measured concentration of the at least one substance, (ii) the different points in time that the concentration of the at least one substance was measured, and (iii) the particular quantity of the at least one of a) glucose and b) insulin added to the extracorporeal blood circuit;
    outputting, using the blood treatment apparatus, a result of the characterizing; and
    detecting diabetes or a pathological glucose tolerance of the patient based on the result of the characterizing.

9. The method according to claim 8, further comprising: changing a dialysate glucose concentration while monitoring the measured concentration.

10. The method according to claim 9, wherein a change in the dialysate glucose concentration is used for determination of at least one characteristic figure relating to the characterizing the patient's metabolization of the particular quantity of the at least one or a) glucose and b) insulin.

11. The method according to claim 9, further comprising:
  determining the glucose shift across the dialysis filter after the adding of the particular quantity of at least one of a) glucose and b) insulin, wherein the glucose shift across the dialysis filter is used for determination of at least one characteristic figure relating to the characterizing the patient's metabolization of the particular quantity of the at least one or a) glucose and b) insulin.

12. The method according to claim 8, wherein at least one of a) the addition of the particular quantity of at least one of glucose and insulin, and b) the measuring the concentration of at least one substance comprised of at least one of glucose and insulin is automated.

13. The method according to claim 8, further comprising:
  displaying at least one determined characteristic figure relating to the result of the characterizing.

14. A hemodialysis, hemofiltration, or hemodiafiltration system, comprising:
  an extracorporeal blood circuit for circulating blood of a patient during a hemodialysis, hemofiltration, or hemodiafiltration treatment;
  a dialysate circuit for circulating dialysate liquid during the hemodialysis, hemofiltration, or hemodiafiltration treatment;
  a dialyzer comprising a dialyzer membrane and defining a blood chamber in fluid communication with the extracorporeal blood circuit and a dialysate chamber in fluid communication with the dialysate circuit;
  a measurement instrument configured to extracorporeally measure, at different points in time during the hemodialysis, hemofiltration, or hemodiafiltration treatment, at least one of glucose concentration and insulin concentration of the blood of the patient at one or more locations along the extracorporeal blood circuit;
  a first input line configured for extracorporeally adding at least one of glucose and insulin during the hemodialysis, hemofiltration, or hemodiafiltration treatment to the extracorporeal blood circuit to mix with the blood of the patient;
  a second input line configured for adding at least one of glucose and insulin to the dialysate circuit such that a glucose shift or an insulin shift across the dialyzer membrane is reduced;
  a blood treatment apparatus configured for characterizing the patient's metabolization of a particular quantity of glucose or insulin added to the extracorporeal blood circuit based on: (i) glucose or insulin concentrations measured by the measurement instrument, (ii) differing points in time at which the glucose or insulin concentrations were measured by the measurement instrument, and (iii) the particular quantity of glucose or insulin added to the extracorporeal blood circuit; and
  an output for providing a result of the characterizing.

15. The system according to claim 14, wherein the blood treatment apparatus is configured to change a dialysate glucose concentration while monitoring the measured glucose concentration.

16. The system according to claim 15, wherein the blood treatment apparatus is configured to calculatorily reflect a change in a determination of at least one characteristic figure relating to the patient's metabolization of the particular quantity of glucose or insulin.

17. The system according to claim 14, wherein the blood treatment apparatus is:
  configured to determine a glucose shift across the dialysis membrane after an extracorporeal addition of glucose; and
  configured to calculatorily reflect the glucose shift across the dialysis membrane in the determination of the at least one characteristic figure relating to the patient's metabolization of the particular quantity of glucose or insulin.

18. The system according to claim 14, wherein the first input line is configured for extracorporeally adding the at least one of glucose and insulin into a substituate supply.

19. The system according to claim 14, wherein the system is automated to at least one of a) add at least one of glucose and insulin and b) measure at least one of the glucose concentration and the insulin concentration.

20. The system according to claim 14, further comprising:
  a display configured for displaying at least one determined characteristic figure relating to the patient's metabolization of the particular quantity of glucose or insulin.

21. The system according to claim 14, wherein the blood treatment apparatus comprises a dialysis apparatus.

22. A hemodialysis, hemofiltration, or hemodiafiltration system, comprising:
  a measurement instrument configured to measure, at different points in time during a hemodialysis, hemofiltration, or hemodiafiltration treatment, a concentration of at least one substance comprised of at least one of a) glucose and b) insulin in blood of a patient at one or more locations along an extracorporeal blood circuit of the system;
  a first input line configured for extracorporeally adding at least one substance comprised of at least one of a) glucose and b) insulin to the extracorporeal blood circuit to mix with the blood of the patient;
  a second input line configured for adding at least one of a) glucose and b) insulin to a dialysate circuit of the system such that a glucose shift or an insulin shift across a dialyzer membrane of the system is reduced;
  a blood treatment apparatus configured for characterizing the patient's metabolization of a particular quantity of glucose or insulin added to the extracorporeal blood circuit by evaluation of a curve over time that is based on: (i) the concentration of the at least one substance measured by the measurement instrument, (ii) the different points in time that the concentration of the at least one substance was measured by the measurement instrument, and (iii) the particular quantity of glucose or insulin added to the extracorporeal blood circuit; and
  an output for providing a result of the characterizing.

23. The system according to claim 22, wherein the blood treatment apparatus is:
  configured to change a dialysate glucose concentration while monitoring the measured glucose concentration.

24. The system according to claim 23, wherein the blood treatment apparatus is:
  configured to calculatorily reflect a change in a determination of at least one characteristic figure relating to the patient's metabolization of the particular quantity of glucose or insulin.

25. The system according to claim 22, wherein the blood treatment apparatus is:
  configured to determine a glucose shift across the dialysis membrane after the extracorporeal addition of the particular quantity of glucose or insulin; and
  configured to calculatorily reflect the glucose shift across the dialysis membrane in the determination of at least one characteristic figure relating to the patient's metabolization of the particular quantity of glucose or insulin.

26. The system according to claim 22, wherein the system is automated to at least one of a) add at least one of glucose and insulin and b) measure at least one of the glucose concentration and the insulin concentration.

27. The system according to claim 22, further comprising:
a display configured for displaying at least one determined characteristic figure relating to the patient's metabolization of the particular quantity of glucose or insulin.

28. The system according to claim 22, wherein the blood treatment apparatus comprises a dialysis apparatus.

* * * * *